US00PP30468P2

(12) United States Plant Patent
Nishikawa

(10) Patent No.: US PP30,468 P2
(45) Date of Patent: Apr. 30, 2019

(54) ***BIDENS* PLANT NAMED '15S25'**

(50) Latin Name: *Bidens triplinervia*
Varietal Denomination: 15S25

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 0 days.

(21) Appl. No.: 15/732,272

(22) Filed: Oct. 17, 2017

(51) Int. Cl.
*A01H 5/02* (2018.01)

(52) U.S. Cl.
USPC ..... Plt./410
CPC ..... *A01H 5/02* (2013.01)

(58) Field of Classification Search
USPC ..... Plt./410
CPC ..... A01H 5/02
See application file for complete search history.

(56) References Cited

PUBLICATIONS http://ehrnet.com/wordpress/wp-content/uploads/2017/06/2017-Spring-Trials-Report-web-version-6-23-17.pdf; 2017; 28 pages.*
https://conceptplants.com/varieties/bidens-beezar-funny-honey-15-s-25/; 2018; 1 page.*

* cited by examiner

*Primary Examiner* — Kent L Bell
(74) *Attorney, Agent, or Firm* — Penny J. Aguirre

(57) ABSTRACT

A new cultivar of *Bidens* named '15S25' that is characterized by its very compact plant habit, and its inflorescences that are orange-yellow in color.

2 Drawing Sheets

Botanical classification: *Bidens triplinervia.*
Variety denomination: '15S25'.

CROSS REFERENCE TO A RELATED APPLICATION

This application is co-pending with a U.S. Plant Patent Application filed for a plant derived from the same breeding program that is entitled *Bidens* Plant Named '15S27' (U.S. Plant patent application Ser. No. 15/732,266).

BACKGROUND OF THE INVENTION

The present invention relates to a new and distinct cultivar of *Bidens triplinervia* plant, botanically of hybrid origin and known as *Bidens* '15S25' and will be referred to hereinafter by its cultivar name, '15S25'. The new cultivar of *Bidens* is an herbaceous perennial grown for landscape and container use.

'15S25' arose from crosses made by the Inventor in Quito, Equador between unnamed and unpatented proprietary plants of *Bidens triplinervia* from his breeding program. The seeds were pooled from the crosses and therefore the exact parents are unknown. '15S25' was selected in 2014 as a single unique plant amongst the resulting seedlings.

Asexual propagation of the new cultivar was first accomplished by stem cuttings under the direction of the Inventor in 2014 in Quito, Equador. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish '15S25' as a unique cultivar of *Bidens*.

1. '15S25' exhibits a very compact plant habit.
2. '15S25' exhibits inflorescences that are orange-yellow in color.

'15S25' can be most closely compared to *Bidens* cultivars 'Florbikano' (U.S. Plant Pat. No. 25,087) and '15S27'. 'Florbikano' differs from '15S25' in having a less compact plant habit and inflorecences that are smaller in size. '15S27' is similar to '15S25' in having a very compact plant habit. '15S27' differs from '15S25' in having red inflorescences.

BRIEF DESCRIPTION OF THE DRAWINGS

The accompanying colored photographs illustrate the overall appearance and distinct characteristics of the new *Bidens*. The photographs were taken of a 3 month-old plant of '15S25' as grown in an unheated greenhouse in a 13-cm container in Boskoop, The Netherlands.

The photograph in FIG. 1 provides a side view of '15S25' and shows the plant habit in bloom.

Figure 1:
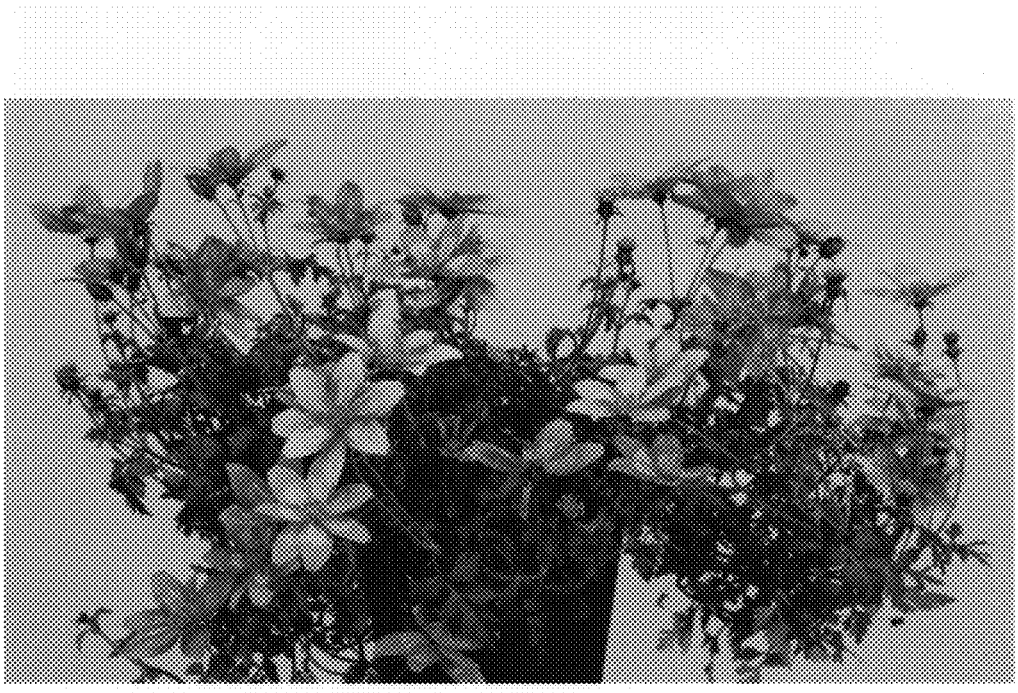
Figure 2:
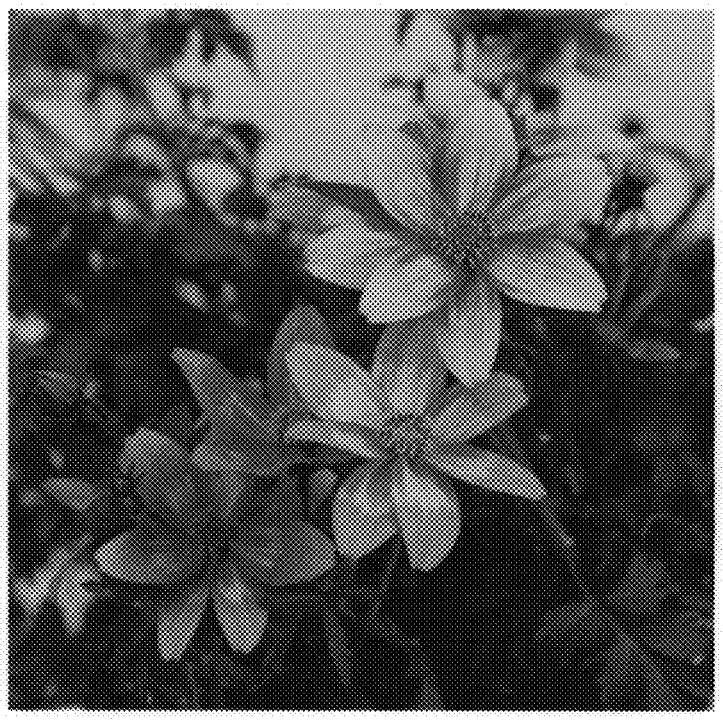

The photograph in FIG. 2 provides a close-up view of the inflorecences of '15S25'.

Figure 3:
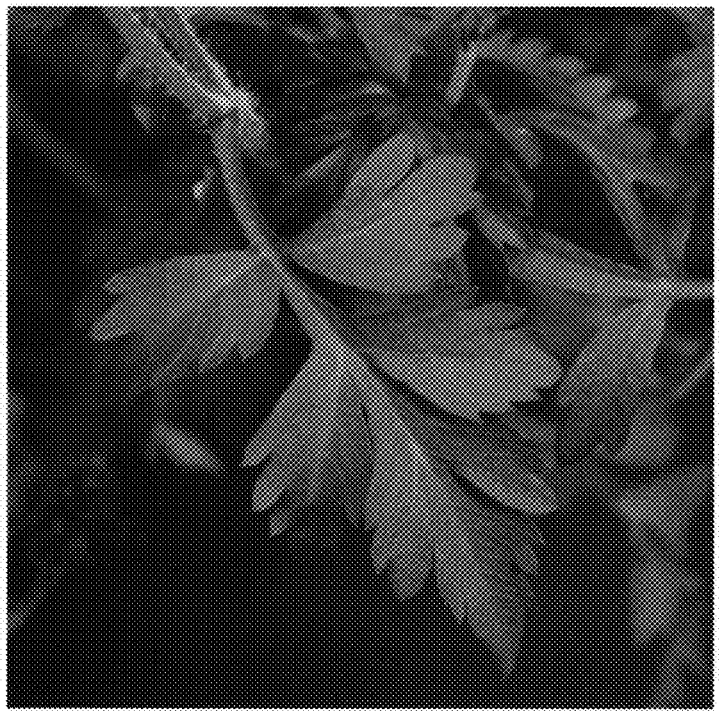

The photograph in FIG. 3 provides a close-up view of the foliage of '15S25'.

The colors in the photographs are as close as possible with the photographic and printing technology utilized and the color values cited in the detailed botanical description accurately describe the colors of the new *Bidens*.

DETAILED BOTANICAL DESCRIPTION

The following is a detailed description of 3 month-old plants of '15S25' as grown in 13-cm containers in an unheated greenhouse in Boskoop, The Netherlands. The phenotype of the new cultivar may vary with variations in environmental, climatic, and cultural conditions, as it has not been tested under all possible environmental conditions.

The color determination is in accordance with The 2015 R.H.S. Colour Chart of The Royal Horticultural Society, London, England, except where general color terms of ordinary dictionary significance are used.

General description:

*Blooming period*.—Blooms from late May until November in Boskoop, The Netherlands.

*Plant type*.—Herbaceous perennial.

*Plant habit*.—Clump-forming, compact, mounding, upright leafy flowering stems with inflorescences held above the foliage.

*Height and spread*.—An average of 11.6 cm (from soil level to uppermost stem leaf), 16.3 cm (from soil level to top of inflorescences), 46.8 cm in width as a 3-month old plant as grown in a 13-cm container.

*Cold hardiness*.—At least to U.S.D.A Zones 9 to 11.

*Diseases and pests*.—No susceptibility and resistance to pests and diseases has been observed.

*Root description*.—Fibrous and fine.

*Propagation*.—Stem cuttings.

*Root development*.—About 2 weeks to initiation roots and 3 weeks to root as a young plant as a liner in summer.

*Growth rate*.—Moderately vigorous.

Stem description:

*Shape*.—Rounded, very slightly angled.

*Stem color*.—Young, 177A, mature 176B.

*Stem size*.—An average of 16.9 cm in length and 2.5 mm in diameter.

*Stem surface*.—Moderately glossy, stems densely covered with short soft hairs, average of 0.8 mm in length, very minute in size, but closest to NN155D in color.

*Stem strength*.—Strong.

*Stem aspect*.—Held at an average angle of 85°.

*Branching habit*.—Lateral branches grow from a single main stem, an average of 6 lateral branches.

*Internode length*.—An average of 3.2 cm.

Foliage description:

*Leaf division*.—Single.

*Leaf arrangement*.—Opposite.

*Leaf attachment*.—Petiolate.

*Leaf petioles*.—An average of 1.5 cm in length, 1 mm in diameter, medium strength, upper surface; 177A in color, slightly glossy and moderately covered with short soft hairs, average of 0.8 mm in length, very minute in size, but closest to NN155D in color, lower surface; 148B to 148C in color, slightly glossy and glabrous.

*Leaf shape*.—Whole leaf and leaflet; ovate.

*Leaf quantity*.—Whole leaf; about 10 per lateral branch, lobes; 3 per leaf.

*Leaf margins*.—Whole leaf; deeply incised, lobes coarsely crenate-serrate.

*Leaf lobes*.—Terminal lobe occasionally lobed, medium to deep sinuses, convergent orientation.

*Leaf size*.—Whole leaf; An average of 3.5 cm in length and 3.4 cm in width, lobes; side lobes 1.7 cm in length and 1.2 cm in width, terminal lobe 2.8 cm in length and 1.8 cm in width.

*Leaf base*.—Whole leaf and lobes; attenuate.

*Leaf apex*.—Whole leaf and lobes; acute.

*Leaf venation*.—Whole leaf and lobes; pinnate, upper surface 146B to 146C, lower surface 143A to 143B.

*Leaf surface*.—Upper surface smooth, matte and glabrous, lower surface smooth, matte and sparsely covered with very short hairs an average of 0.5 mm in length, very minute in size, but closest to 157D in color.

*Leaf color*.—Young upper surface 137B, young lower surface 138B, mature upper surface between 137A and 137B, mature lower surface 138B.

Flower description:

*Inflorescence type*.—Terminal and axillary capitulums, upright.

*Lastingness of inflorescence*.—Average of 2 weeks, discs persistent, ray florets self-cleaning.

*Fragrance*.—Faint sweet scent.

*Quantity of inflorescences*.—Free flowering, with an average of 70 inflorescences per plant.

*Inflorescence size*.—An average of 1.7 cm in height, 5.8 cm in diameter.

*Inflorescence buds*.—Ovate in shape, an average of 1.4 cm in depth and 8 mm in diameter (excluding the involucral bracts), smooth and glossy surface, color; NN137B, immature ray florets N167B.

*Peduncle*.—Rounded in shape, strong, an average of 6.2 cm in length and 1 mm in diameter, 138A to 138B in color, surface is slightly glossy and sparsely pubescent covered with short soft hairs, average of 0.5 mm in length, very minute in size, but closest to NN155D in color.

Involucral bracts:

*Involucral number*.—Two rows of 10.

*Involucral arrangement*.—Spirally placed around involucrum.

*Involucral size*.—An average of 7 mm in length, 1.5 mm in width.

*Involucral color*.—Fully open upper and lower surface; NN137A.

*Involucral texture*.—Upper surface glabrous and smooth, lower surface moderately pubescent with short soft hairs, average of 0.8 mm in length, very minute in size, but closest to NN155D in color.

*Involucral apex*.—Acute.

*Involucral base*.—Broad cuneate.

*Involucral shape*.—Lanceolate.

Ray florets (no reproductive organs):

*Number*.—7, an average of 2 rows (whorls).

*Shape*.—Ovate, slightly carinate.

*Size*.—An average of 3 cm in length and 1.45 cm in width.

*Apex*.—Praemorse.

*Base*.—Attenuate.

*Margins*.—Entire, undulation is low.

*Aspect*.—Nearly horizontal to slightly upward, an average angle of 15° to horizontal.

*Texture*.—Upper surface; glabrous, matte, smooth and velvety, lower surface; glabrous, matte, smooth and very slightly velvety.

*Color*.—When opening upper surface N163B, base between 42A and 179A with conspicuous blotches on the lower half 14A, when opening lower surface is a blend of N167A, N167B and N167C, when fully open upper surface N163C, base 9A, base margins 169A to 169B, when fully open lower surface a blend of 22A and 163B and 163C.

Disc florets:

*Number*.—An average of 50, average of 5 rows (whorls).

*Shape*.—Tubular, lower 92% fused into tube, free tips.

*Aspect*.—Upright.

*Size*.—Average of 1.1 cm in length and 1.25 mm in width.

*Apex*.—Acute.

*Margins*.—Entire.

*Texture*.—Upper surface moderately glossy, lower surface glossy, both surfaces smooth and glabrous.

*Color*.—Upper and lower surface when opening and fully open; 15A.

*Receptacle*.—An average of 6 mm in depth, 4 mm in width, 145D in color.

*Receptacle spines*.—A single receptacle spine is placed next to each individual disc floret, acicular in shape, 7 mm in length, 0.6 mm in diameter, acute apex, cuneate base, smooth and glabrous surfaces, color; apex 11A, very top of tip 197B, mid-section and base 145D.

Reproductive organs:

*Presence*.—Disc flowers only.

*Gynoecium*.—1 Pistil, an average of 6 mm in length, stigma; decurrent, reflexed, 0.8 mm in length, 1.5 mm in diameter, 17B in color, style; 5.2 mm, 16C to 16D in color, ovary; 145B to 145C in color.

*Androecium*.—5 stamens, an average of 2 mm in length and 0.3 mm in width, 200A in color, anther; basifixed, linear, 2 mm in length, 0.3 mm in width, 200A in color, filament; 3 mm in length, 150C to 150D in color, pollen; low in quantity, 17A to 17B in color.

*Seed*.—No seed development has observed observed to date.

It is claimed:

1. A new and distinct cultivar of *Bidens* plant named '15S25' as herein illustrated and described.

* * * * *